(12) United States Patent
El-Baz et al.

(10) Patent No.: US 11,481,905 B2
(45) Date of Patent: Oct. 25, 2022

(54) ATLAS FOR AUTOMATIC SEGMENTATION OF RETINA LAYERS FROM OCT IMAGES

(71) Applicant: University of Louisville Research Foundation, Inc., Louisville, KY (US)

(72) Inventors: Ayman S. El-Baz, Louisville, KY (US); Ahmed Soliman, Louisville, KY (US); Ahmed Eltanboly, Louisville, KY (US); Ahmed Sleman, Louisville, KY (US); Robert S. Keynton, Goshen, KY (US); Harpal Sandhu, Louisville, KY (US); Andrew Switala, Louisville, KY (US)

(*) Notice: Subject to any disclaimer, the term of this patent is extended or adjusted under 35 U.S.C. 154(b) by 32 days.

(21) Appl. No.: 17/050,269

(22) PCT Filed: Apr. 26, 2019

(86) PCT No.: PCT/US2019/029278
§ 371 (c)(1),
(2) Date: Oct. 23, 2020

(87) PCT Pub. No.: WO2019/210124
PCT Pub. Date: Oct. 31, 2019

(65) Prior Publication Data
US 2021/0082123 A1   Mar. 18, 2021

Related U.S. Application Data (60) Provisional application No. 62/663,011, filed on Apr. 26, 2018.

(51) Int. Cl.
*G06K 9/00* (2022.01)
*G06T 7/143* (2017.01)

(52) U.S. Cl.
CPC .... *G06T 7/143* (2017.01); *G06T 2207/10101* (2013.01); *G06T 2207/20128* (2013.01); *G06T 2207/30041* (2013.01)

(58) Field of Classification Search
CPC ........... G06T 7/143; G06T 2207/10101; G06T 2207/20128; G06T 2207/30041
See application file for complete search history.

(56) References Cited

U.S. PATENT DOCUMENTS

| | | | |
|---|---|---|---|
| 2005/0196026 A1* | 9/2005 | Klingensmith | A61B 8/0858 382/128 |
| 2008/0193006 A1 | 8/2008 | Udupa et al. | |

(Continued)

FOREIGN PATENT DOCUMENTS

WO   2017/149315   8/2017

OTHER PUBLICATIONS

W. Weng, Y. Liang, E. S. Kimball, T. Hobbs, S. X. Kong, B. Sakurada, and J. Bouchard, "Decreasing incidence of type 2 diabetes mellitus in the united states, 20072012: Epidemiologic findings from a large us claims database," Diabetes Research and Clinical Practice, vol. 117, No. Supplement C, pp. 111-118, 2016. [Online]. Available: http://www.sciencedirect.com/science/article/pii/S0168822716301073.

(Continued)

*Primary Examiner* — Atiba O Fitzpatrick
(74) *Attorney, Agent, or Firm* — Dentons Bingham Greenebaum LLP; Brian W. Chellgren (57) ABSTRACT

A method for segmentation of a 3-D medical image uses an adaptive patient-specific atlas and an appearance model for 3-D Optical Coherence Tomography (OCT) data. For segmentation of a medical image of a retina, In order to reconstruct the 3-D patient-specific retinal atlas, a 2-D slice of the 3-D image containing the macula mid-area is segmented first. A 2-D shape prior is built using a series of co-aligned training OCT images. The shape prior is then adapted to the first order appearance and second order spatial interaction MGRF model of the image data to be segmented. Once the macula mid-area is segmented into (Continued)

separate retinal layers this initial slice, the segmented layers' labels and their appearances are used to segment the adjacent slices. This step is iterated until the complete 3-D medical image is segmented.

17 Claims, 6 Drawing Sheets

(56) References Cited

U.S. PATENT DOCUMENTS

| | | |
|---|---|---|
| 2017/0105616 A1 | 4/2017 | Lowry et al. |
| 2017/0109883 A1 | 4/2017 | Lowry et al. |
| 2017/0132793 A1* | 5/2017 | Hu .......................... G06T 5/20 |
| 2018/0082443 A1 | 3/2018 | Risman et al. |

OTHER PUBLICATIONS

M. D. Abramoff, M. K. Garvin, and M. Sonka, "Retinal imaging and image analysis," IEEE Reviews in Biomedical Engineering, vol. 3, pp. 169-208, 2010.
D. Huang, E. A. Swanson, C. P. Lin, J. S. Schuman, W. G. Stinson, W. Chang, M. R. Hee, T. Flotte, K. Gregory, C. A. Puliafito et al., "Optical coherence tomography," Science (New York, NY), vol. 254, No. 5035, p. 1178, 1991.
A. Prakash, M. O. Macias, M. Hewko, M. Sowa, and S. Sherif, "Vascular plaque detection with reduced textural feature set from optical coherence tomography images," in Photonics North (PN), 2016. IEEE, 2016, pp. 1-1.
H. Soltanizadeh and S. R. Oshterinan, "A new method for automatic lumen detection in intracoronary oct images," in Biomedical Engineering (ICBME), 2014 21th Iranian Conference on. IEEE, 2014, pp. 186-189.
C. Chen, V. C. Kavuri, X. Wang, R. Li, H. Liu, and J. Huang, "Multi-frequency diffuse optical tomography for cancer detection," in Biomedical Imaging (ISBI), 2015 IEEE 12th International Symposium on. IEEE, 2015, pp. 67-70.
A. Stankiewicz, T. Marciniak, A. Dbrowski, M. Stopa, E. Marciniak, and A. Michalski, "Matching 3d oct retina images into super-resolution dataset," in 2016 Signal Processing: Algorithms, Architectures, Arrange-ments, and Applications (SPA), Sep. 2016, pp. 130-137.
M. Shen, L. Cui, M. Li, D. Zhu, M. R. Wang, and J. Wang, "Extended scan depth optical coherence tomography for evaluating ocular surface shape," Journal of biomedical optics, vol. 16, No. 5, pp. 056 007-056 007, 2011.
D. Williams, Y. Zheng, F. Bao, and A. Elsheikh, "Fast segmentation of anterior segment oct images using graph cut," Eye and Vision, vol. 2, No. 1, p. 1, 2015.
F. LaRocca, S. J. Chiu, A. N. Kuo, J. A. Izatt, and S. Farsiu, "Robust automatic segmentation of corneal layer boundaries in oct images using graph theory and dynamic programming," Investigative Ophthalmology & Visual Science, vol. 52, No. 14, pp. 4182-4182, 2011.
V. A. Robles, B. J. Antony, D. R. Koehn, M. G. Anderson, and M. K. Garvin, "3d graph-based automated segmentation of corneal layers in anterior-segment oct images of mice," in SPIE Medical Imaging, vol. 9038. International Society for Optics and Photonics, 2014, p. 90380F.

J. A. Eichel, K. K. Bizheva, D. A. Clausi, and P. W. Fieguth, "Automated 3d reconstruction and segmentation from optical coherence tomography," in European Conference on Computer Vision. Springer, 2010, pp. 44-57.
D. Williams, Y. Zheng, P. G. Davey, F. Bao, M. Shen, and A. Elsheikh, "Reconstruction of 3d surface maps from anterior segment optical co-herence tomography images using graph theory and genetic algorithms," Biomedical Signal Processing and Control, vol. 25, pp. 91-98, 2016.
F. Rathke, S. Schmidt, and C. Schnrr, "Probabilistic intra-retinal layer segmentation in 3-d oct images using global shape regularization," Medical Image Analysis, vol. 18, No. 5, pp. 781-794, 2014. [Online]. Available: http://www.sciencedirect.com/science/article/pii/S1361841514000449.
M. K. Garvin, M. D. Abra'moff, X. Wu, S. R. Russell, T. L. Burns, and M. Sonka, "Automated 3-d intraretinal layer segmentation of macular spectral-domain optical coherence tomography images," IEEE transac-tions on medical imaging, vol. 28, No. 9, pp. 1436-1447, 2009.
K. L. P. S. P. G. Y. K. M. N. Z. H. M. K. G. Bhavna J. Antony, Michael D. Abrmoff, "Automated 3d segmentation of intraretinal layers from optic nerve head optical coherence tomography images," pp. 7626-7626—12, 2010. [Online]. Available: http://dx.doi.org/10.1117/12.843928.
L. Fang, S. Li, D. Cunefare, and S. Farsiu, "Segmentation based sparse reconstruction of optical coherence tomography images," IEEE transactions on medical imaging, vol. 36, No. 2, pp. 407-421, 2017.
J. Lim et al., "A direct method for modeling non-rigid motion with thin plate spline," in CVPR 2005., 2005, pp. 1196-1202.
Q. Yang et al., "Automated layer segmentation of macular oct images using dual-scale gradient information," Opt. Express, vol. 18, No. 20, pp. 21 293-21 307, 2010.
A. El-Baz et al., "Precise segmentation of 3-D magnetic resonance angiography," vol. 59, No. 7, pp. 2019-2029, 2012.
T. K. Moon, "The expectation-maximization algorithm," IEEE Signal Processing Magazine, vol. 13, No. 6, pp. 47-60, Nov. 1996.
N. Liu, G. Gimel'farb, and P. Delmas, "High-order mgrf models for contrast/offset invariant texture retrieval," in Proceedings of the 29th International Conference on Image and Vision Computing New Zealand. ACM, 2014, pp. 96-101.
K. Li, X. Wu, D. Z. Chen, and M. Sonka, "Optimal surface segmentation in volumetric images—a graph-theoretic approach," IEEE transactions on pattern analysis and machine intelligence, vol. 28, No. 1, pp. 119-134, 2006.
B. Antony, M. D. Abramoff, L. Tang, W. D. Ramdas, J. R. Vingerling, N. M. Jansonius, K. Lee, Y. H. Kwon, M. Sonka, and M. K. Garvin, "Automated 3-d method for the correction of axial artifacts in spectral-domain optical coherence tomography images," Biomedical optics ex-press, vol. 2, No. 8, pp. 2403-2416, 2011.
International Search Report and Written Opinion, dated Jul. 12, 2019 for International Patent application No. PCT/US19/29278, for applicant University of Louisville Research Foundation, Inc.
Bai Fangliang et al. "Superpixel guided active contour segmentation of retinal layers in OCT volumes" Progress in Biomedical Optics and Imaging, SPIE—International Society for Optical Engineering, Bellingham, WA, US, vol. 10591, Mar. 5, 2018.
Supplementary European Search Report for EP 19792925 to University of Louisville Research Foundation, dated Dec. 7, 2021.

* cited by examiner

ATLAS FOR AUTOMATIC SEGMENTATION OF RETINA LAYERS FROM OCT IMAGES

This application claims the benefit of U.S. provisional patent application Ser. No. 62/663,011, filed 26 Apr. 2018, for ATLAS FOR AUTOMATIC SEGMENTATION OF RETINA LAYERS FROM OCT IMAGES, incorporated herein by reference.

FIELD OF THE INVENTION

A method for segmentation of a 3-D medical image uses an adaptive patient-specific atlas and an appearance model for 3-D Optical Coherence Tomography (OCT) data. For segmentation of a medical image of a retina, In order to reconstruct the 3-D patient-specific retinal atlas, a 2-D slice of the 3-D image containing the macula mid-area is segmented first. A 2-D shape prior is built using a series of co-aligned training OCT images. The shape prior is then adapted to the first order appearance and second order spatial interaction MGRF model of the image data to be segmented. Once the macula mid-area is segmented into separate retinal layers in this initial slice, the segmented layers' labels and their appearances are used to segment the adjacent slices. This step is iterated until the complete 3-D medical image is segmented.

BACKGROUND

There are approximately 415 million adults living with diabetes worldwide and approximately 642 million could be affected by 2040. Those affected are at risk for degraded vision due to diabetic retinopathy, in which damage to the blood vessels leads to fluid accumulation in the retinal layers. It is crucial to monitor and detect changes in the morphology and appearance of retinal layers in order to prevent loss of vision in diabetic patients. There are several medical imaging modalities that can be used to observe qualitative and quantitative anatomical features of the retina, such as fundus imaging and optical coherence tomography (OCT). Fundus imaging produces a 2-D representation of the retina where the reflected amount of light is represented by image intensities. Fundus imaging is limited in that it does not provide any indication of depth, i.e. the particular layers of retina where changes occur. OCT overcomes this limitation with the ability to noninvasively image internal tissue of the human body in cross section at micron resolutions through measuring the reflections of light waves. OCT is used heavily by ophthalmologists and optometrists for obtaining high-resolution images of the retina and anterior segment of the eye. The modality has found widespread application such as vascular plaque detection, lumen detection, and cancer detection.

A volumetric OCT scan includes of a set of A-scans representing reflectivity of retinal tissue as a function of depth beneath a single point on the surface. The juxtaposition of A-scans taken along a line across the surface provides a cross-sectional image or B-scan, a 2-D medical image. Volumetric OCT, a 3-D medical image, comprises an array of adjacent B-scans. To be able to quantify both the morphology and reflectivity of a certain layer of retina, a user must segment the volume into layers and extract the layer of interest from the volume. The typical method to extract the layer of interest is to use image editing software to manually delineate retinal layers. However, this method is time consuming, subjective, and dependent on the experience and skill of the individual performing the manual segmentation.

Several approaches to automatic segmentation have been proposed. Most can be classified as: 1) threshold methods, 2) level set based techniques, and 3) graph cut techniques. However, the existing techniques suffer from at least one of several limitations: 1) segmentation of retinal layers is derived from only a single B-scan (e.g., a cross section of the macula), 2) coarse segmentation of the retina into fewer than the approximately 12 layers that can be distinguished by OCT, and 3) long execution times, particularly for graph-based approaches, rendering the automatic segmentation techniques unsuitable for clinical use.

SUMMARY

To address these limitations, disclosed herein is a novel, fast, patient-specific approach to segmentation of OCT retinal image data that includes selecting a B-scan extending through the center of the fovea, segmenting the slice into a plurality of retinal layers, then using the obtained segmentation data to drive the segmentation of adjacent B-scans recursively. This approach is able to segment all 12 layers of retina and, to the best of the inventors' knowledge, will be the first fast 3-D segmentation approach with such capabilities which makes it suitable for a clinical setting.

This new approach uses patient-specific anatomy of retinal layers to accurately segment the retinal image. The accuracy and speed of the instant 3-D segmentation approach is highlighted by comparing results with those generated by a state-of-the-art 3-D OCT segmentation approach. Extracting the patient-specific atlas that describes both anatomy and appearance/reflectivity from the central OCT image and propagating this atlas to segment the adjacent images results in increased speed and accuracy as compared to existing techniques. While the proposed approach was developed to segment OCT images, its underlying concept can be generalized to segment organs from other 3-D medical imaging modalities such as CT and MRI.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
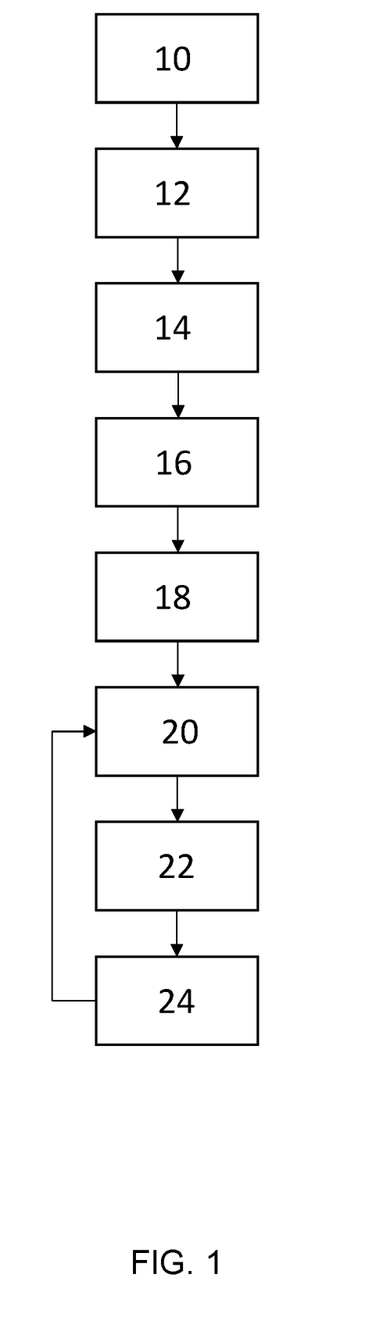
FIG. 1 is a flowchart illustrating a method for OCT 3-D macular volume segmentation.

Referring now to FIG. 1, the depicted novel framework possesses the ability to accurately segment 13 distinct surfaces, namely, 12 retinal layers, as well as the vitreous and the choroid, from OCT volumes. The proposed framework proceeds into two stages: stage 1, an algorithmic 2-D segmentation of the B-scan extending through the center of the fovea (also referred to as the midline B-scan, macula mid-slice, or the initial slice), then stage 2, where the inherited segmentation information from the midline B-scan image propagates outward from the midline B-scan image to aid segmentation of the entire 3-D volume as explained in Section B. In further detail, a method for segmentation of medical images includes 10 —providing a 3-D medical image (e.g., a 3D-OCT retinal image), 12—selecting an initial 2-D slice of the 3-D medical image, preferably at or near the center of the 3-D image (e.g, a slice bisecting the foveal pit), 14—aligning the initial image slice to a constructed shape database (e.g., a database comprising different fovea images collected from different healthy and diseased subjects), 16—applying a joint model to the aligned initial image slice, and 18—obtaining a final segmentation of the initial slice (e.g., segmenting the 12 of layers of the retina in the initial slice). Steps 12 through 18 comprise the first stage. Continuing to the second stage, the method 10 includes 20—selecting a current image slice adjacent to the previously segmented image slice, 22—aligning the current image slice to the previously segmented image slice image, and 24—segmenting the current image slice based at least in part upon the previously segmented image slice. Steps 20 through 24 comprising the second stage are then repeated to progressively segment the entire volume of the medical image. Once segmented, the plurality of 2-D slices may be reassembled into a 3-D image for convenient visualization of the segmented image. Steps of the first stage and second stage are described in further detail in sections A and B, respectively.

A. Joint MGRF Based Macula-Centered Foveal Image Segmentation

Let $g=\{g(x):x \in R; g(x) \in Q\}$ and $m=\{l(x):x \in R; l(x) \in L\}$ be a grayscale image taking values from Q, i.e., $g:R \rightarrow Q$, with the associated region map taking values from L, i.e., $m:R \rightarrow L$, respectively. R denotes a finite arithmetic lattice, Q is a finite set of integer gray values, and L is a set of region labels. An input OCT image, g, co-aligned to the training database, and its map, m, are described with a joint probability model:

$$P(g,m)=P(g|m)P(m)$$

which combines a conditional distribution of the images given the map $P(g|m)$, and an unconditional probability distribution of maps $P(m)=P_{sp}(m)P_v(m)$. Here, $P_{sp}(m)$ denotes a weighted shape prior, and $P_v(m)$ is a Gibbs probability distribution with potentials V, that specifies a MGRF model of spatially homogeneous maps m.

(1) Shape Model $P_{sp}(m)$: In order to account for the inhomogeneity of the OCT images, the shape information is incorporated in the segmentation process. The shape model is constructed using OCT scans selected in such a way as to be representative and to capture the biological variability of the whole data set. "Ground truth" segmentations of these scans were delineated under supervision of retina specialists. Using one of the optimal scans as a reference (no tilt, centrally located fovea), the others were co-registered using a thin plate spline (TPS). The shape prior was defined as:

$$P_{sp}(m) = \eta \prod_{y \in R} p_{sp:y}(l)$$

Figure 2:
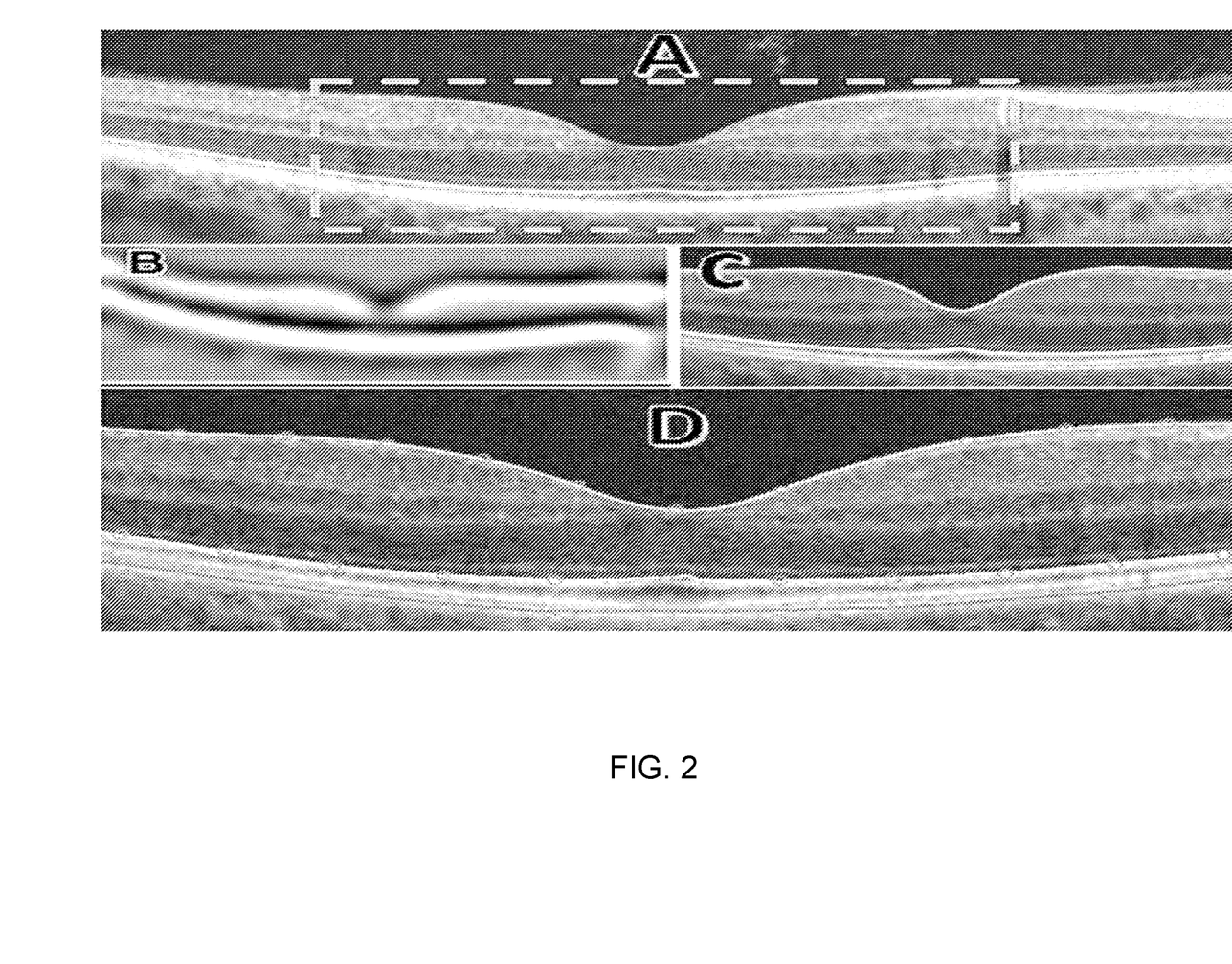
FIG. 2 depicts an alignment procedure for an input OCT image (A), highlighting the large scale structure of the retina in (B). Multiscale edges near the foveal peak, inside the bounded region of (A) are shown in (C). At the finest level of detail, three boundaries are detected (D).

Where, $p_{sp:y}(l)$ is the pixel-wise probability for label l, and y is the image pixel with gray level g. The same deformations were applied to their respective ground truth segmentations, which were then averaged to produce a probabilistic shape prior of the typical retina, i.e., each location x in the reference space is assigned a prior probability P(m) to lie within each of the 12 layers' classes. The same deformations were applied to their respective ground truth segmentations, then averaged to produce a probabilistic shape prior of the typical retina. The input medical image intended to be segmented (i.e., the initial slice) is first aligned to the shape database. The used alignment approach integrates TPS with the multi-resolution edge tracking method that identifies control points for initializing the alignment process as shown in FIG. 2. More specifically, a coarse detail component of the undecimated discrete wavelet transform is used to locate changes in OCT reflectivity, where one zone transitions into another. The sharpest zone boundaries in the normal or mildly pathological retina occur at the vitreous/NFL, ONL/ELM, and RPE/choroid boundaries. The center of the fovea is identified as the point where the vitreous/NFL boundary is at minimal distance from the ONL/ELM boundary. Control points are automatically placed on each boundary at the foveal pit, and outward therefrom at regular intervals. A TPS transformation is used to warp the image, bringing the control points into alignment with the corresponding locations in the retinal atlas.

(2) Adaptive Model: In order to make the segmentation process adaptive and not biased to only the shape information, a 1st-order intensity model P(g|m) was used for the empirical gray level distribution of the OCT images. The visual appearance of each label of the image is modeled by separating a mixed distribution of pixel intensities into individual components associated with the dominant modes of the mixture. The modes are identified using the LCDG algorithm, which employs positive and negative Gaussian components that is based on a modified version of the classical Expectation Maximization (EM) algorithm. Then, a 2nd-order MGRF model $P_v(m)$ is used to improve the spatial homogeneity of the segmentation. This model was identified using the nearest pixels' 8-neighborhood and analytical bi-valued Gibbs potentials V that depend on the equality of the nearest pair of labels. This MGRF Potts model that accounts for spatial information was incorporated with the shape and intensity information as explained in Section A.

B. Layers Segmentation 3-D Propagation

Figure 3:
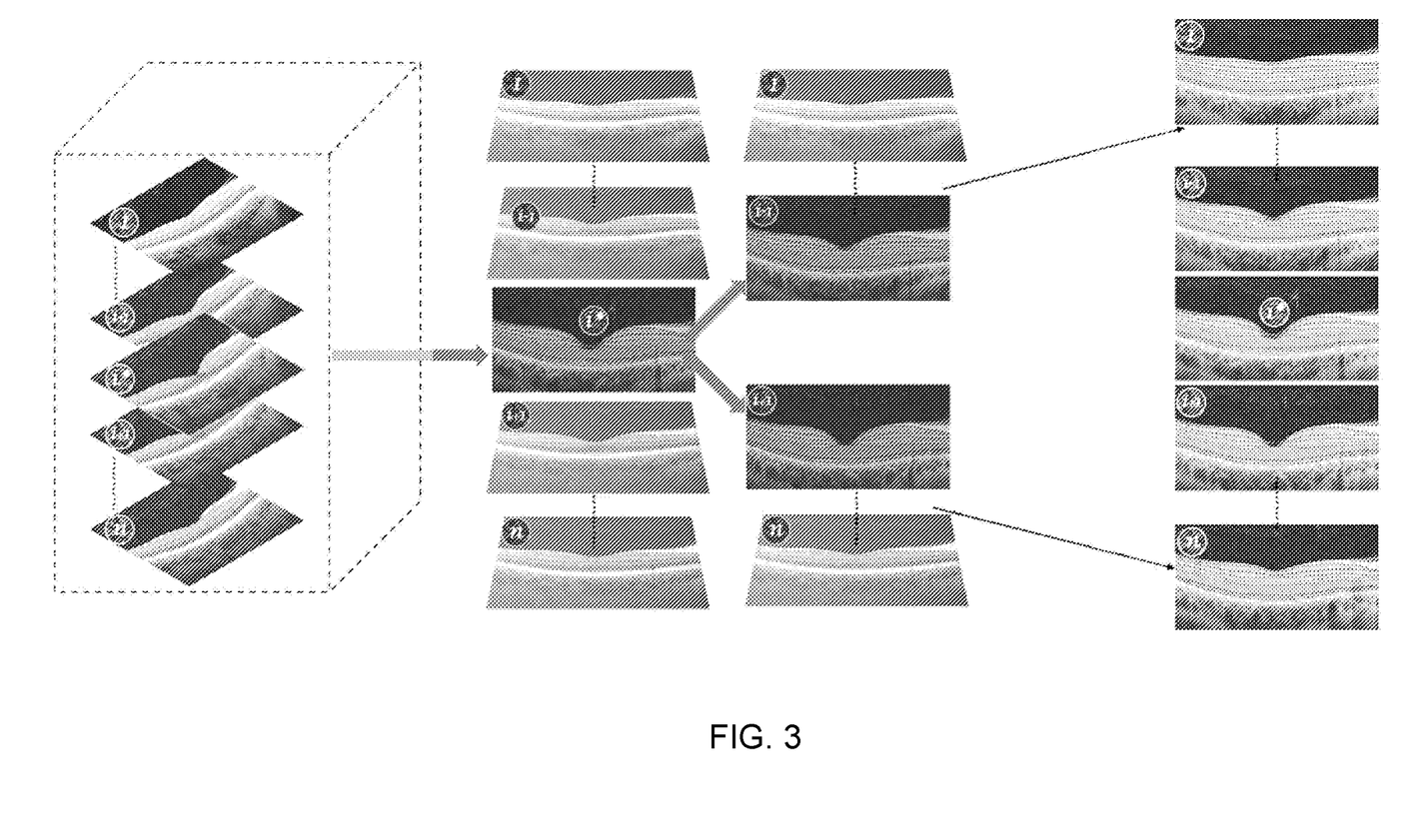
FIG. 3 depicts an illustration of the midline B-scan segmentation propagation process into the whole B-scan volume.

Referring now to FIG. 3, 3-D OCT retinal image data comprises a plurality of 2-D B-scans ranging from 1 to n, as shown in the dashed line enclosure on the left side of the figure. As the inter-subject variability for the retinal cross sections is very high compared to intra-subject variability, the obtained segmentation of the initial midline B-slice, designated as "i" in this figure, is utilized as an initial seed to guide the segmentation of neighboring slices in the ±z-direction. To segment the remaining 3-D slices, a segmentation propagation technique is developed based on a novel adaptive shape prior that takes into account the mapped voxel locations in addition to the reflectivity values, such that B-slices i+1 and i−1 are segmented at least in part based on the segmentation of B-slice i, slice i+2 is segmented at least in part based on the segmentation of slice i+1, slice i+3 is segmented at least in part based on the segmentation of slice i+2, and so forth until all slices 1 to n have been segmented. Unlike traditional shape models that depend only on the mapped voxel location to calculate the probabilistic map, this 1st order adaptive intensity model is designed such that only the visually similar voxels will contribute in the probability map calculations for the slice to be segmented to provide accurate segmentation results.

Figure 4:
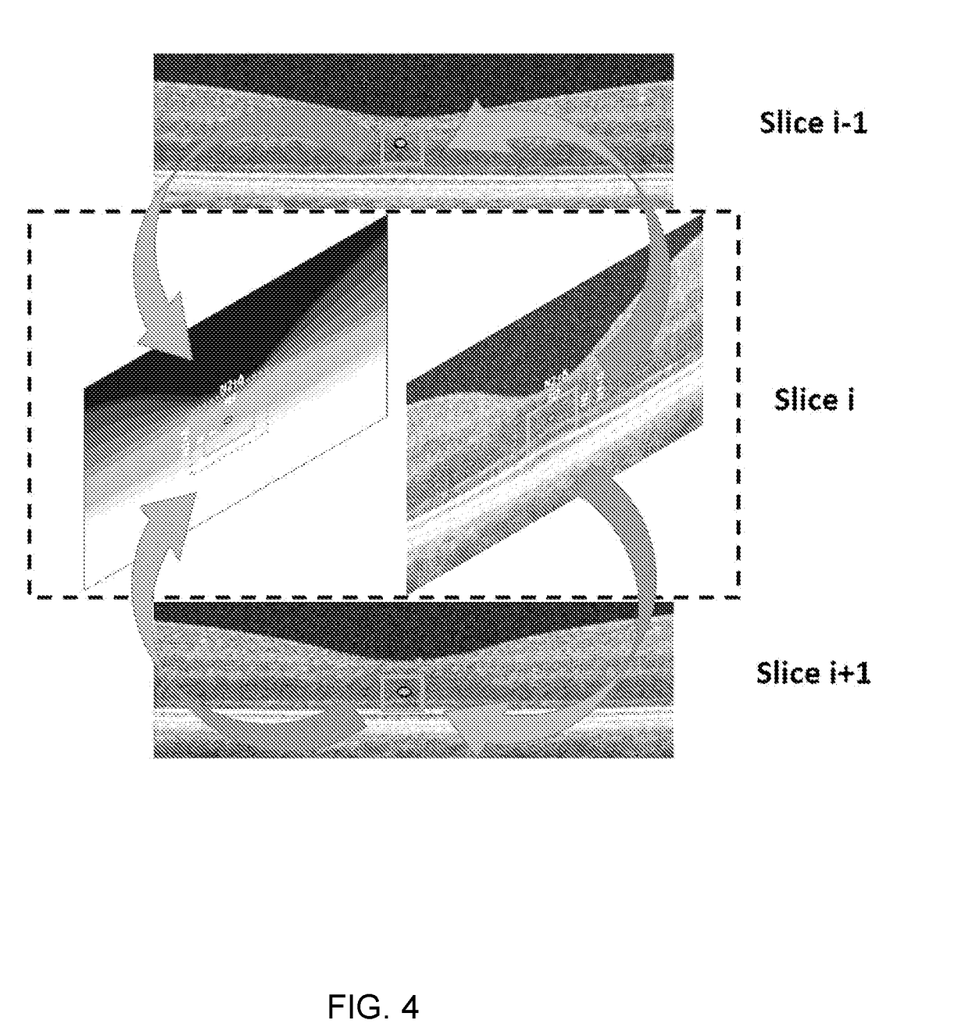
FIG. 4 depicts an illustration of voxel labeling in patient-specific atlas-based (propagation) segmentation process.

Referring now to FIG. 4, the segmentation process proceeds as follows: starting from the initial midline B-slice, the 12 retinal layers will be segmented as described above and assigned different labels, L (L=1 . . . 12). Then moving backward and forward in the z-direction, each current slice i is segmented referring to the previously segmented slice (i+1 or i−1), based on the direction. This procedure comprises first aligning the reflectivity image of the current slice to its previously segmented adjacent neighbor slice to obtain a deformation field that maps each voxel of the current slice to its neighbor. Second, the obtained deformation field is used to map each voxel to its corresponding location at the segmented neighboring slice. Third, at each voxel in the slice i, a N 1×N 2 window w (shown as solid line boxes overlaying the slices in FIG. 4) is generated around its mapped counterpart in adjacent slice (i+1 or i−1), then voxels in that window whose reflectivity values fall within a predefined tolerance ±τ are selected. If no voxels are found, the window size is increased until such voxel(s) are found, or maximum window size is reached (max window size shown as dotted line boxes overlaying the slices). Fourth, the probability of each voxel to be part of a specific layer is calculated based on the occurrence of positively labeled voxels from the total voxels in slice i+1 which are within the window whose reflectivity values are close to the voxel in slice i. Fifth, MGRF spatial refinement is then applied for the obtained initial map for each slice independently to improve the segmentation result. Sixth, the whole volume is finally reconstructed, and 3-D-median filter is applied to the volume which improves the segmentation consistency and surface smoothness. The above procedure is detailed in Algorithm 1.

Algorithm 1: Steps of the Shape Prior Segmentation.
1) Segment the retinal layers in the midline slice following the procedures in Section A.
2) For each slice i, i=1 to n
  I. Use non-rigid registration to align the gray image for the current slice (slice i) with the preceding/succeeding slice (based on the direction) to obtain the deformation fields.
  II. For each pixel v in slice i
    (a) Transform v to the neighboring slice domain using the obtained deformation field.
    (b) Initialize a 2-D window, w, of size $N_{1i} \times N_{2i}$ centered around the mapped voxel ($v_{mapped}$).
    (c) Search w for pixels with corresponding reflectivity value in the neighboring slice where reflectivity falls within a predefined tolerance ±τ in w.
    (d) If no pixels are found using Step (c), increase the size of w and repeat step (c) until correspondences are found or the maximum size allowed for w is reached.
    (e) Calculate the shape probability for each retinal layer at location r based on the found voxels and their labels.
  End for
  III. Assign pixel v the label with the highest probability.
End for For clarification, please note that "slice i" refers to the initial slice in FIG. 3, and refers to the slice currently being segmented in FIG. 4 and Algorithm 1.

EXPERIMENTAL RESULTS: Ten 3-D OCT scans of 10 subjects were used to test the accuracy of the disclosed method of retinal layer segmentation and validate the method against manual segmentation. The OCT scans of the subjects were collected using Zeuss Cirrus HD-OCT 5000 with 5 OCT scans per each OCT volume. Subjects' range of age is from 32 to 50 years (mean±SD, 40±10.2 years). Retina expert specialists manually segmented the scans of retinal layers to construct a ground truth segmentation.

Figure 5:
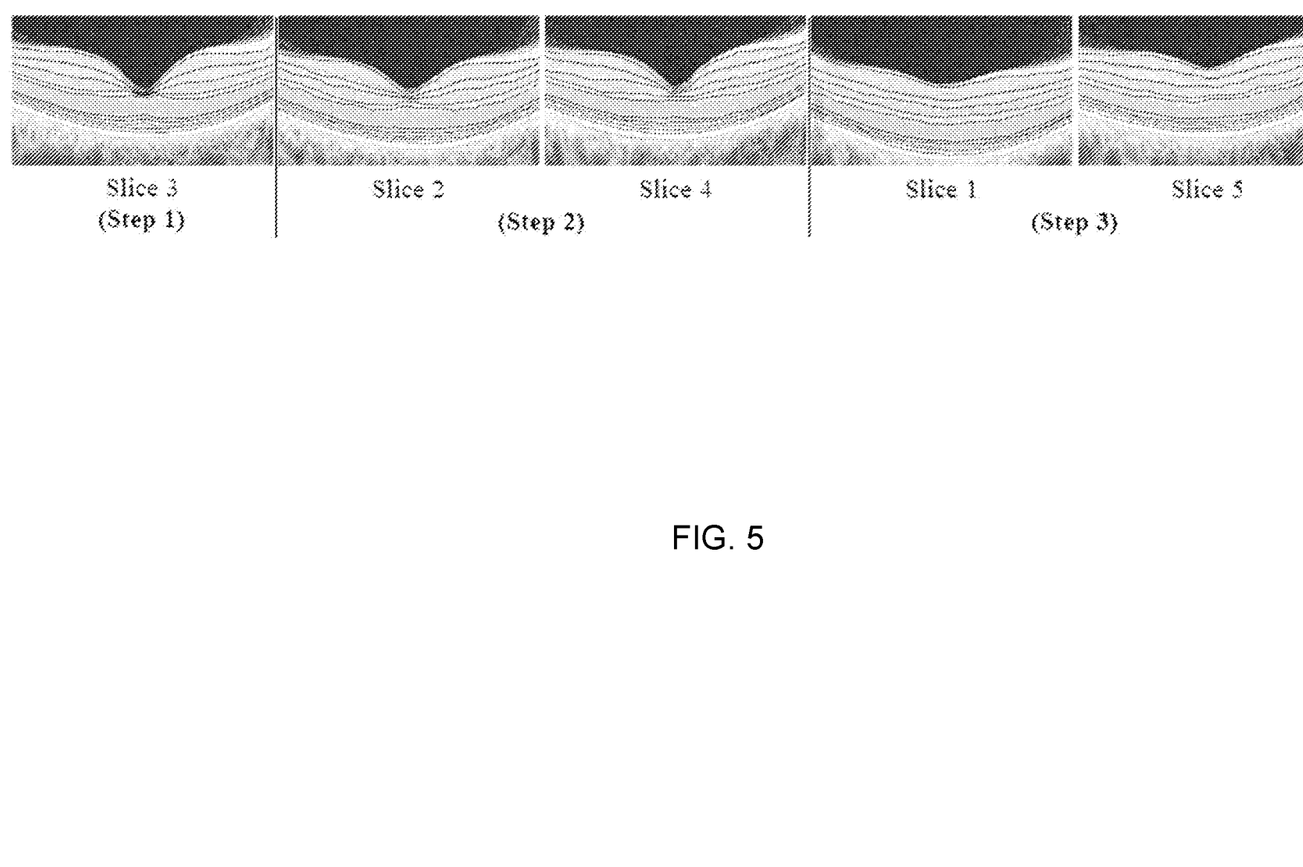
FIG. 5 depicts an illustrative example of the execution steps on a 5-scan 3-D OCT volume showing how macula mid-slice segmentation in (Step 1) is used to drive the segmentation of adjacent slices (Step 2) and the use of resulting segmentation from (Step 2) to drive the segmentation of further adjacent slices (Step 3).

FIG. 5 displays b-slices from a sample 5-scan (i.e., consisting of 5 b-slices) 3-D OCT volume segmented into 12 layers using the disclosed procedure of segmentation. The segmentation process is accomplished in three steps as shown in FIG. 5. The three steps are demonstrated below:

Step 1: Segmentation using joint-MGRF model to obtain the macula mid-slice (slice i, i.e., slice 3 out of 5).

Step 2: 3-D Segmentation propagation using slice i as a patient-specific atlas to segment both slices i−1 and i+1 (i.e., slices 2 and 4).

Step 3: 3-D Segmentation propagation by using slice i−1 (i.e., slice 2) as a patient-specific atlas to segment slice i−2 (i.e., slice 1) and using slice i+1 (i.e., slice 4) as a patient-specific atlas to segment slice i+2 (i.e., slice 5).

As should be readily understood, this process is expandable to any number of slices following the pattern of using a segmented slice as a patient-specific atlas for segmentation of the adjacent slice in the following step. The instant segmentation approach has been found to be reliable for segmentation of challenging diseased cases such as age-related macular degeneration (AMD) and diabetic retinopathy where the layers' anatomy is distorted.

To evaluate the accuracy and robustness of the proposed approach, four commonly used evaluation metrics were used to compare the disclosed segmentation approach with the ground truth and prior work. These metrics are listed below:

(1) Dice Similarity Coefficient (DSC) which is a measure of the ratio of shared segmentation between two images. It can be defined as follows:

$$DSC = \frac{2|R \cap W|}{|R| + |W|}$$

where R and W are the two segmentations to be compared. The higher the DSC value is, the more similar both segmentations are.

(2) 95-percentile bidirectional modified Hausdorff Distance (HD) that measures the maximum distance between 2 matching points for 2 different segmentation techniques. The smaller the distance, the better the segmentation. For two sets of boundary points (X, Y), HD is defined as:

$$HD(X, Y) = \max_{x \in X} [\min_{y \in Y}(|x - y|)]$$

where the 5% largest distances are removed, then the maximum of HD(X, Y) and HD(Y, X) is determined for each image.

(3) Unsigned Mean Surface Position Error (MSPE) that measures the distance between boundaries in two different segmentations at each point across the images.

(4) Average Volume Difference (AVD) which measures the volume difference between obtained segmentation and the ground truth. A smaller volume difference indicates a better segmentation.

In order to highlight the advantage of the approach disclosed herein, it is compared with a well-established 3-D automated segmentation approach as disclosed in Li, K., et al., "Optimal surface segmentation in volumetric images—a graph-theoretic approach," IEEE Transactions on Pattern Analysis and Machine Intelligence, vol. 28, no. 1, pp. 119-134, 2006. However, the approach in Li et al. can only segment 11 of the 12 retinal layers. In order to have a fair comparison, 6th and 7th layers in the 12 retinal layers segmented using the instant approach are merged to make the number of layers equivalent in both techniques.

Figure 6:
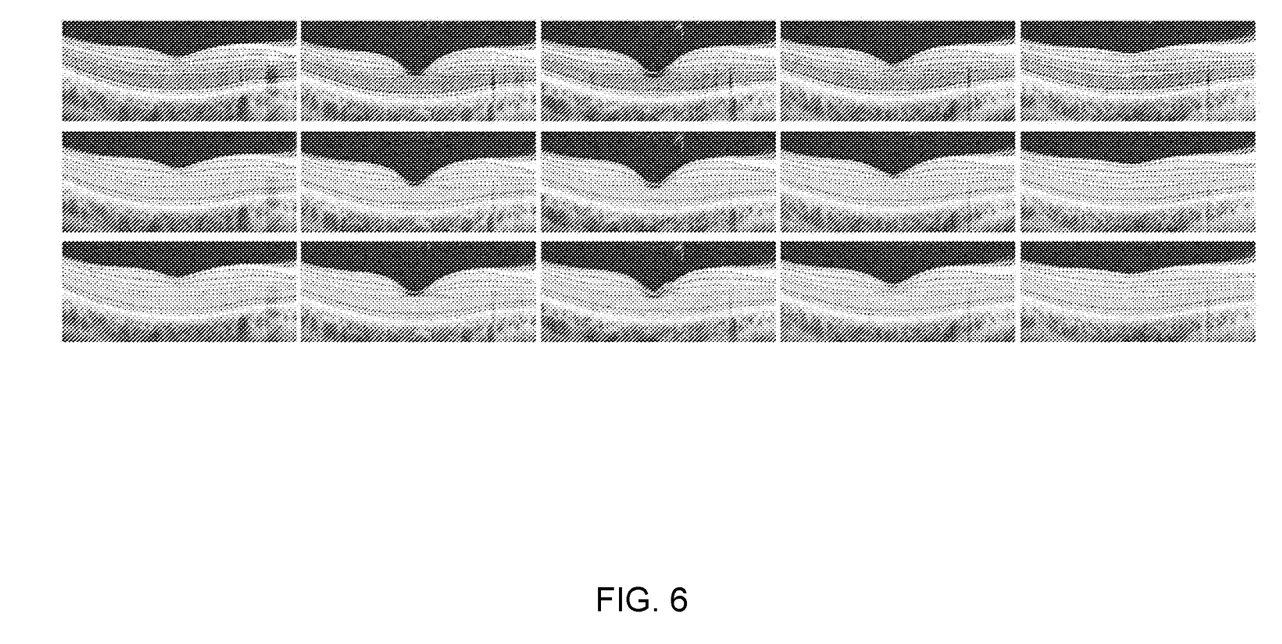
FIG. 6 depicts a comparison of retinal image segmentation generated by (top row) ground truth, (middle row) the disclosed segmentation approach, and (bottom row) a prior art segmentation approach.

FIG. 6 provides a visual comparison of segmentation of five retinal images by ground truth, i.e., by retinal experts (top row), generated using the system disclosed herein (middle row), and generated by the approach of Li et al. (bottom row). Table 1 provides a quantitative evaluation of the results of the instant segmentation approach and Li et al. as compared to ground truth based on four evaluation metrics, DSC, HD, MSPE, and AVD, averaged over all subjects per each layer.

The above results indicate overall superior performance of the instant method in terms of DSC, HD, MSPE, and AVD as compared to the earlier approach disclosed in Li et al. Using paired t-test for statistical analysis shows a significant advantage of this approach over the earlier approach in terms of all metrics as confirmed by p-values <0.05.

Various aspects of different embodiments of the present disclosure are expressed in paragraphs X1 and X2 as follows:

X1: One embodiment of the present disclosure includes a method for segmenting a medical image comprising: receiving a volumetric medical image comprising a plurality of slices, each slice being adjacent to at least one other slice in the image; selecting an initial slice; segmenting the initial slice based at least in part on a constructed shape model; and segmenting at least one slice adjacent to the initial slice based at least in part on the segmented initial slice.

X2: Another embodiment of the present disclosure includes a method for segmenting a 3-D medical image comprising: receiving a 3-D medical image, the 3-D medical image comprising an array of adjacent 2-D medical images; segmenting an initial 2-D medical image based at least in part on a constructed shape model; and segmenting a 2-D medical image adjacent to the previously segmented 2-D medical image based at least in part on the previously segmented 2-D medical image.

Yet other embodiments include the features described in any of the previous paragraphs X1 or X2 as combined with one or more of the following aspects:

Wherein the medical images are retinal images.

Wherein the medical images are optical coherence tomography images.

Wherein the initial slice has two adjacent slices.

Wherein the volumetric medical image is a 3-D medical image and wherein the plurality of slices are a plurality of 2-D medical images.

TABLE 1

Comparative segmentation accuracy between this proposed approach and Li et al., evaluated by DSC, HD, MSPE, and AVD.

| Metric Method | DSC (%) | | HD (voxels) | | MSPE (voxels) | | AVD (%) | |
|---|---|---|---|---|---|---|---|---|
| | Proposed | Li et al. | Proposed | Li et al. | Proposed | Li et al. | Proposed | Li et al. |
| Layer 1 | 82.51 ± 2.91 | 76.32 ± 5.96 | 3.81 ± 0.90 | 8.02 ± 5.54 | 0.16 ± 0.11 | 1.44 ± 0.79 | 15.28 ± 9.73 | 41.17 ± 18.47 |
| Layer 2 | 82.81 ± 2.53 | 77.23 ± 4.34 | 5.41 ± 3.40 | 5.65 ± 3.71 | 0.32 ± 0.15 | 0.72 ± 0.50 | 8.98 ± 3.97 | 6.95 ± 4.19 |
| Layer 3 | 80.36 ± 3.30 | 77.94 ± 4.19 | 8.19 ± 4.28 | 5.02 ± 3.49 | 0.30 ± 0.14 | 0.75 ± 0.44 | 16.22 ± 15.48 | 6.15 ± 3.29 |
| Layer 4 | 80.35 ± 3.30 | 77.80 ± 3.56 | 7.46 ± 3.72 | 4.02 ± 1.77 | 0.46 ± 0.24 | 0.50 ± 0.28 | 8.91 ± 5.94 | 14.39 ± 3.16 |
| Layer 5 | 78.93 ± 3.51 | 76.77 ± 3.58 | 15.33 ± 6.07 | 5.92 ± 3.27 | 1.86 ± 0.82 | 1.24 ± 0.44 | 22.41 ± 16.02 | 35.64 ± 14.87 |
| Layer 6 | 84.64 ± 3.72 | 81.77 ± 2.15 | 3.33 ± 2.52 | 2.06 ± 0.55 | 0.83 ± 0.37 | 0.23 ± 0.09 | 11.04 ± 5.55 | 5.28 ± 4.18 |
| Layer 7 | 84.51 ± 3.74 | 80.89 ± 2.13 | 3.60 ± 4.68 | 6.62 ± 1.18 | 0.55 ± 0.68 | 1.85 ± 0.34 | 20.91 ± 14.48 | 31.60 ± 3.34 |
| Layer 8 | 84.42 ± 3.71 | 80.04 ± 2.22 | 3.25 ± 2.65 | 7.34 ± 0.96 | 0.26 ± 0.17 | 2.57 ± 0.58 | 20.25 ± 10.51 | 24.48 ± 14.24 |
| Layer 9 | 84.10 ± 4.00 | 79.49 ± 2.26 | 4.20 ± 2.42 | 7.95 ± 1.77 | 1.02 ± 0.78 | 2.48 ± 0.93 | 56.73 ± 63.79 | 36.89 ± 5.03 |
| Layer 10 | 83.70 ± 4.11 | 79.08 ± 15.51 | 4.79 ± 1.59 | 14.28 ± 5.59 | 0.94 ± 0.63 | 1.17 ± 0.40 | 26.61 ± 14.44 | 73.24 ± 10.74 |
| Layer 11 | 83.31 ± 4.06 | 78.08 ± 15.07 | 3.15 ± 0.29 | 13.13 ± 4.93 | 1.29 ± 1.99 | 2.27 ± 1.27 | 15.92 ± 12.48 | 41.80 ± 15.75 |
| Average | 82.69 ± 3.37 | 78.67 ± 4.72 | 5.68 ± 1.90 | 7.27 ± 2.01 | 0.73 ± 0.21 | 1.38 ± 0.35 | 20.30 ± 11.94 | 28.87 ± 2.93 |

Wherein segmenting the initial slice includes aligning the initial slice to the constructed shape model.

Wherein segmenting the initial slice further includes applying a joint model to the initial slice subsequent to alignment.

Wherein segmenting the at least one slice adjacent to the initial slice includes aligning the at least one slice to the initial slice.

Further comprising, after segmenting the initial slice, applying a label to each segmented layer in the initial slice.

Wherein each segmented layer corresponds to a retinal layer.

Wherein segmenting the at least one slice adjacent to the initial slice based at least in part on the segmented initial slice includes, for a pixel in the at least one slice, transforming the pixel to the initial slice, initializing a window, searching within the window for pixels with a corresponding value in the initial slice, and calculating a shape prior probability based on the labels of found pixels with corresponding values, and labeling the pixel in the at least one slice based on the shape prior probability.

Wherein the pixel in the at least one slice has a reflectivity value and wherein searching within the window for pixels with the corresponding value in the initial slice comprises searching within the window for pixels with corresponding reflectivity values in the initial slice.

Further comprising, after the step of segmenting the 2-D medical image, repeating the prior step until all 2-D medical images in the array are segmented.

Wherein the 3-D medical image is a retinal image depicting at least a fovea, and wherein the initial 2-D medical image extends through the fovea.

Wherein segmenting the initial 2-D medical image includes aligning the initial 2-D medical image to the constructed shape model and applying a joint model to the initial 2-D medical image subsequent to alignment.

Wherein the initial 2-D medical image depicts an anatomical feature and wherein the constructed shape model is constructed from a database of images of the anatomical feature.

Wherein the anatomical feature is a fovea.

Wherein segmenting the 2-D medical image based at least in part on the previously segmented 2-D medical image includes, for a pixel in the 2-D medical image, determining a value for the pixel, transforming the pixel to the previously segmented 2-D medical image, initializing a window, searching within the window for pixels with a corresponding value in the previously segmented 2-D medical image, calculating a shape prior probability based on labels of found pixels with corresponding values, and labeling the pixel in the 2-D medical image based on the shape prior probability.

Wherein the value for the pixel is a reflectivity value for the pixel.

The foregoing detailed description is given primarily for clearness of understanding and no unnecessary limitations are to be understood therefrom for modifications can be made by those skilled in the art upon reading this disclosure and may be made without departing from the spirit of the invention. While the disclosed invention has been described primarily in connection with the segmentation of 3-D OCT retinal images, it should be understood that the disclosed segmentation techniques may be usable with segmentation of 3-D medical images obtained using different imaging modalities or depicting different anatomical features.

What is claimed is:

1. A method for segmenting a medical image comprising:
receiving a volumetric medical image comprising a plurality of slices, each slice being adjacent to at least one other slice in the image;
selecting an initial slice;
segmenting the initial slice based at least in part on a constructed shape model;
applying a label to each segmented layer in the initial slice; and
segmenting at least one slice adjacent to the initial slice based at least in part on the segmented initial slice
wherein segmenting the at least one slice adjacent to the initial slice based at least in part on the segmented initial slice includes, for a pixel in the at least one slice, transforming the pixel to the initial slice, initializing a window, searching within the window for pixels with a corresponding value in the initial slice, and calculating a shape prior probability based on the labels of found pixels with corresponding values, and labeling the pixel in the at least one slice based on the shape prior probability.

2. The method of claim 1, wherein the medical images are retinal images.

3. The method of claim 1, wherein the medical images are optical coherence tomography images.

4. The method of claim 1, wherein the initial slice has two adjacent slices.

5. The method of claim 1, wherein the volumetric medical image is a 3-D medical image and wherein the plurality of slices are a plurality of 2-D medical images.

6. The method of claim 1, wherein segmenting the initial slice includes aligning the initial slice to the constructed shape model.

7. The method of claim 6, wherein segmenting the initial slice further includes applying a joint model to the initial slice subsequent to alignment.

8. The method of claim 1, wherein segmenting the at least one slice adjacent to the initial slice includes aligning the at least one slice to the initial slice.

9. The method of claim 1, wherein each segmented layer corresponds to a retinal layer.

10. The method of claim 1, wherein the pixel in the at least one slice has a reflectivity value and wherein searching within the window for pixels with the corresponding value in the initial slice comprises searching within the window for pixels with corresponding reflectivity values in the initial slice.

11. A method for segmenting a 3-D medical image comprising:
receiving a 3-D medical image, the 3-D medical image comprising an array of adjacent 2-D medical images;
segmenting an initial 2-D medical image based at least in part on a constructed shape model; and
segmenting a 2-D medical image adjacent to the segmented initial 2-D medical image based at least in part on the segmented initial 2-D medical image
wherein segmenting the 2-D medical image based at least in part on the previously segmented 2-D medical image includes, for a pixel in the 2-D medical image, determining a value for the pixel, transforming the pixel to the previously segmented 2-D medical image, initializing a window, searching within the window for pixels with a corresponding value in the previously segmented 2-D medical image, calculating a shape prior probability based on labels of found pixels with corresponding values, and labeling the pixel in the 2-D medical image based on the shape prior probability.

12. The method of claim 11, further comprising, after the step of segmenting the 2-D medical image, repeating the step of segmenting the 2-D medical image until all 2-D medical images in the array are segmented.

13. The method of claim 11, wherein the 3-D medical image is a retinal image depicting at least a fovea, and wherein the initial 2-D medical image extends through the fovea.

14. The method of claim 11, wherein segmenting the initial 2-D medical image includes aligning the initial 2-D medical image to the constructed shape model and applying a joint model to the initial 2-D medical image subsequent to alignment.

15. The method of claim 11, wherein the initial 2-D medical image depicts an anatomical feature and wherein the constructed shape model is constructed from a database of images of the anatomical feature.

16. The method of claim 15, wherein the anatomical feature is a fovea.

17. The method of claim 11, wherein the value for the pixel is a reflectivity value for the pixel.

* * * * *